(12) United States Patent
Govari et al.

(10) Patent No.: US 11,832,883 B2
(45) Date of Patent: Dec. 5, 2023

(54) USING REAL-TIME IMAGES FOR AUGMENTED-REALITY VISUALIZATION OF AN OPHTHALMOLOGY SURGICAL TOOL

(71) Applicant: JOHNSON & JOHNSON SURGICAL VISION, INC., Irvine, CA (US)

(72) Inventors: Assaf Govari, Haifa (IL); Vadim Gliner, Haifa (IL)

(73) Assignee: JOHNSON & JOHNSON SURGICAL VISION, INC., Irvine, CA (US)

( * ) Notice: Subject to any disclaimer, the term of this patent is extended or adjusted under 35 U.S.C. 154(b) by 0 days.

(21) Appl. No.: 16/856,696

(22) Filed: Apr. 23, 2020

(65) Prior Publication Data

US 2021/0330393 A1    Oct. 28, 2021

(51) Int. Cl.
| | | |
|---|---|---|
| G09G 5/00 | (2006.01) | |
| A61B 3/10 | (2006.01) | |
| A61B 34/10 | (2016.01) | |
| A61B 34/20 | (2016.01) | |
| G06T 7/38 | (2017.01) | |
| G02B 27/01 | (2006.01) | |
| G06T 7/00 | (2017.01) | |

(Continued)

(52) U.S. Cl.
CPC .......... *A61B 3/10* (2013.01); *A61B 1/000094* (2022.02); *A61B 34/10* (2016.02); *A61B 34/20* (2016.02); *G02B 27/017* (2013.01); *G06T 7/0012* (2013.01); *G06T 7/38* (2017.01); *G06T 19/003* (2013.01); *G06T 19/006* (2013.01); *A61B 2034/102* (2016.02); *A61B 2034/107* (2016.02); *A61B 2034/2057* (2016.02); *A61B 2034/2059* (2016.02); *A61B 2034/2074* (2016.02); *G06T 2207/10081* (2013.01); *G06T 2207/30041* (2013.01); *G06T 2210/41* (2013.01); *G06T 2211/428* (2013.01)

(58) Field of Classification Search
CPC ....... G06T 19/006; G06T 19/00; G06F 3/011; G06F 3/012; G02B 27/017
USPC ....................................................... 345/633
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |

(Continued)

FOREIGN PATENT DOCUMENTS

| | | |
|---|---|---|
| EP | 0951874 A2 | 10/1999 |
| EP | 1829477 A2 | 9/2007 |

(Continued)

*Primary Examiner* — Gordon G Liu
(74) *Attorney, Agent, or Firm* — Johnson & Johnson Surgical Vision, Inc.

(57) ABSTRACT

A system includes a processor and a display. The processor is configured to: (a) receive, from a camera inserted into an eye of a patient, at least an optical image of at least a region-of-interest (ROI) of the eye, (b) receive, from a position tracking system (PTS), a position signal indicative of a position of a medical instrument treating the eye, (c) register the optical image and the PTS in a common coordinate system, and (d) estimate the position of the medical instrument in the optical image. The display is configured to visualize at least the ROI and the medical instrument.

18 Claims, 3 Drawing Sheets

(51) Int. Cl.
*G06T 19/00* (2011.01)
*A61B 1/00* (2006.01)

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,498,944 B1 | 12/2002 | Ben-Haim et al. |
| 6,618,612 B1 | 9/2003 | Acker et al. |
| 6,690,963 B2 | 2/2004 | Ben-Haim et al. |
| 8,180,430 B2 | 5/2012 | Govari et al. |
| 10,638,080 B2 | 4/2020 | Ovchinnikov et al. |
| 2002/0065455 A1 | 5/2002 | Ben-Haim et al. |
| 2003/0023161 A1 | 1/2003 | Govari et al. |
| 2003/0120150 A1 | 6/2003 | Govari |
| 2004/0068178 A1 | 4/2004 | Govari |
| 2004/0199072 A1 | 10/2004 | Sprouse et al. |
| 2005/0203380 A1 | 9/2005 | Sauer et al. |
| 2006/0281971 A1 | 12/2006 | Sauer et al. |
| 2007/0265526 A1 | 11/2007 | Govari et al. |
| 2013/0015848 A1 | 1/2013 | Govari et al. |
| 2013/0060146 A1 | 3/2013 | Yang et al. |
| 2013/0245461 A1 | 9/2013 | Maier-Hein et al. |
| 2014/0275760 A1 | 9/2014 | Lee et al. |
| 2015/0272694 A1 | 10/2015 | Charles |
| 2015/0327948 A1 | 11/2015 | Schoepp et al. |
| 2015/0366628 A1 | 12/2015 | Ingmanson |
| 2016/0015469 A1 | 1/2016 | Goshayesh |
| 2017/0007155 A1 | 1/2017 | Gliner |
| 2017/0007156 A1 | 1/2017 | Govari et al. |
| 2017/0172696 A1 | 6/2017 | Saget et al. |
| 2017/0280989 A1* | 10/2017 | Heeren ................ A61B 3/0058 |
| 2017/0367771 A1* | 12/2017 | Tako .................... G06T 19/003 |
| 2018/0068441 A1 | 3/2018 | Yu et al. |
| 2018/0098816 A1 | 4/2018 | Govari et al. |
| 2018/0220100 A1 | 8/2018 | Ovchinnikov et al. |
| 2018/0228392 A1 | 8/2018 | Govari et al. |
| 2018/0245461 A1 | 8/2018 | Barak |
| 2018/0270436 A1* | 9/2018 | Ivarsson ................ G06V 40/19 |
| 2018/0286132 A1 | 10/2018 | Cvetko et al. |
| 2019/0058859 A1* | 2/2019 | Price .................... H04N 13/271 |
| 2019/0083115 A1 | 3/2019 | Bar-Tal |
| 2019/0192232 A1 | 6/2019 | Altmann et al. |
| 2019/0365346 A1 | 12/2019 | Elliot et al. |
| 2020/0015923 A1 | 1/2020 | Scheib |
| 2020/0188173 A1* | 6/2020 | Berlin ................. A61F 9/00802 |
| 2021/0196105 A1* | 7/2021 | Algawi .............. A61B 1/00114 |
| 2021/0330394 A1 | 10/2021 | Govari et al. |
| 2021/0330395 A1 | 10/2021 | Govari et al. |
| 2021/0330396 A1 | 10/2021 | Govari et al. |

FOREIGN PATENT DOCUMENTS

| | | |
|---|---|---|
| EP | 2829218 A1 | 1/2015 |
| EP | 3400871 A1 | 11/2018 |
| EP | 3387984 B1 | 4/2020 |
| EP | 3241051 B1 | 6/2020 |
| WO | 9605768 A1 | 2/1996 |
| WO | 2019141704 A1 | 7/2019 |
| WO | 2021076560 A1 | 4/2021 |

* cited by examiner

USING REAL-TIME IMAGES FOR AUGMENTED-REALITY VISUALIZATION OF AN OPHTHALMOLOGY SURGICAL TOOL

FIELD OF THE INVENTION

The present invention relates generally to medical devices, and particularly to methods and systems for tracking and visualizing medical instruments in ophthalmic procedures.

BACKGROUND OF THE INVENTION

During a minimally invasive medical procedure, such as an ophthalmic surgical procedure, a surgeon navigates a medical instrument to a target location within a patient eye. In some cases, patient tissue may obstruct from the surgeon's view, at least part of the medical instrument. Various techniques have been developed for tracking and visualizing medical instruments during minimally invasive procedures.

For example, U.S. Patent Publication No. 2018/0220100 describes a system including an augmented reality device communicatively coupled to an imaging system of an ophthalmic microscope. The augmented reality device may include a lens configured to project a digital image, a gaze control configured to detect a focus of an eye of an operator, and a dimming system communicatively coupled to the gaze control and the outer surface. The system including a processor that receives a digital image from the imaging system, projects the digital image on the lens, receives a signal from the gaze control regarding the focus of the eye of the operator, and transitions the outer surface of the augmented reality device between at least partially transparent to opaque based on the received signal.

U.S. Patent Publication No. 2013/0060146 describes systems and methods for surgical guidance and image registration, in which three-dimensional image data associated with an object or patient is registered to topological image data obtained using a surface topology imaging device. The surface topology imaging device may be rigidly attached to an optical position measurement system that also tracks fiducial markers on a movable instrument. The instrument may be registered to the topological image data, such that the topological image data and the movable instrument are registered to the three-dimensional image data. The three-dimensional image data may be CT or MRI data associated with a patient. The system may also co-register images pertaining to a surgical plan with the three-dimensional image data.

U.S. Patent Publication No. 2013/0245461 describes a sensor means employed to sense a distance to the surface of a subject to be examined, so that a range image may be acquired. Intensity information may be acquired alongside the distance information. The distance information and intensity information may be evaluated to track the pose of the sensor means relative to the surface of the subject to be examined, so that anatomical data related to said subject may be displayed as seen from the position and/or orientation of the sensor means or display means. By moving the sensor means or display means along the surface of the subject to be examined, such as a patient in a hospital environment, the user hence gets the impression of being able to look directly into the human body.

U.S. Patent Publication No. 2015/0366628 describes a system including an image capture device to capture an image of a surgical environment. At least one biometric sensor obtains biometric data from a patient. A controller includes a memory configured to store a plurality of anatomical images and a processor. The processor receives at least one of the captured image, the biometric data, or one or more anatomical images from the plurality of anatomical images and generates an augmented image from at least one of the captured image, the biometric data, or the one or more anatomical images. A display device displays the augmented image.

SUMMARY OF THE INVENTION

An embodiment of the present invention that is described herein provides a system including a processor and a display. The processor is configured to: (a) receive, from a camera inserted into an eye of a patient, at least an optical image of at least a region-of-interest (ROI) of the eye, (b) receive, from a position tracking system (PTS), a position signal indicative of a position of a medical instrument treating the eye, (c) register the optical image and the PTS in a common coordinate system, and (d) estimate the position of the medical instrument in the optical image. The display is configured to visualize at least the ROI and the medical instrument.

In some embodiments, the optical image includes a real-time (RT) image. In other embodiments, the camera is coupled with the medical instrument and further comprising a second camera coupled to a tool for inserting the second camera into the eye, and the at least optical image includes at least one of (a) a first optical image received from the first camera and (b) a second optical image received from the second camera. In yet other embodiments, the processor is configured to receive at least an anatomical image of at least the ROI, and when at least part of the medical instrument is obstructed by a blocking element in at least one of the anatomical image and the optical image, the processor is configured to display the position of the medical instrument unobstructed.

In an embodiment, when at least part of the medical instrument is obstructed, the processor is configured to visualize the medical instrument overlaid on at least one of the anatomical image and the optical image. In another embodiment, the anatomical image includes at least one of: (i) an optical-based anatomical image, and (ii) a computerized tomography-based anatomical image. In yet another embodiment, the display includes an augmented reality display configured to display an augmented reality image, and the processor is configured to simultaneously display, on the augmented reality display, the optical image on a first section of the augmented reality image, and the anatomical image on a second section of the augmented reality image.

In some embodiments, (i) when at least part of the medical instrument is obstructed in the anatomical image, the processor is configured to display the ROI and the medical instrument of the optical image, and (ii) when at least part of the medical instrument is obstructed in the optical image, the processor is configured to display the ROI and the medical instrument of the anatomical image. In other embodiments, when at least part of the medical instrument is obstructed in the anatomical image and in the optical image, the processor is configured, based on the position signal, to visualize the estimated position of the obstructed part of the anatomical image, in at least one of the anatomical image and the optical image. In yet other embodiments, the common coordinate system includes a coordinate system of the PTS.

There is additionally provided, in accordance with an embodiment of the present invention, a method including receiving, from a camera inserted into an eye of a patient, at least an optical image of at least a region-of-interest (ROI) of the eye. A position signal indicative of a position of a medical instrument treating the eye, is received from a position tracking system (PTS). The optical image and the PTS are registered in a common coordinate system. The position of the medical instrument is estimated in the optical image, and at least the ROI and the medical instrument are visualized.

The present invention will be more fully understood from the following detailed description of the embodiments thereof, taken together with the drawings in which:

DETAILED DESCRIPTION OF EMBODIMENTS

Overview

Accurate position tracking and visualization of a medical instrument are particularly important in surgical procedures carried out in small organs, such as in a patient eye. Embodiments of the present invention that are described hereinbelow provide improved techniques for tracking and visualizing a medical instrument, which is at least partially obstructed or hidden from view to a surgeon during an ophthalmic surgical procedure.

In some embodiments, an ophthalmic surgical system comprises a location pad, which is configured to be attached to facial tissue surrounding at least part of a patient eye. In some embodiments, the location pad comprises multiple field-generators of a position tracking system (PTS), which are coupled to the frame at respective positions surrounding at least a portion of the eye and are configured to generate respective magnetic fields at least in a region-of-interest (ROI) of the patient eye.

In some embodiments, the ophthalmic surgical system comprises a medical instrument, such as a surgical tool, having one or more position sensor(s) of the PTS, which is coupled to the surgical tool, for example in an embodiment, the sensor is coupled with the distal end of the surgical tool, and is configured to sense the magnetic fields. In response to sensing the magnetic fields, the position sensor is configured to produce a position signal indicative of the position of the surgical tool, such as the distal end in the ROI.

In some embodiments, the ophthalmic surgical system comprises at least one of (i) a first camera, coupled to a distal end of the surgical tool, and (ii) a second camera, coupled to an insertion tool for inserting the second camera, at a different position, into the patient eye. The first and second cameras are configured to generate real-time (RT) images of the distal end in the ROI.

In some embodiments, the ophthalmic surgical system comprises a processor, which is configured to receive one or more of (a) the one or more RT images, (b) at least an anatomical image, such as a computerized tomography-based anatomical image (CTI) or an optical-based anatomical image (OAI), of the patient eye, and (c) a position signal indicative of the position of the surgical tool (e.g. the distal end thereof) in the ROI. The processor is further configured to register at least one of the RT images and at least one of the anatomical images in a coordinate system of the PTS, and to estimate the position of the surgical tool in at least one of the RT images and anatomical images. The processor is further configured to produce an augmented reality image comprising at least one of the RT images displayed on the ROI, and at least one of the anatomical images displayed on one or more sections surrounding the ROI.

In some embodiments, the ophthalmic surgical system comprises an augmented reality (AR) display, which is configured to visualize to the surgeon, at least the ROI and the distal end of the surgical tool. In some cases, eye tissue or any other blocking element, may obstruct a portion of the surgical tool. For example, the distal end may be obstructed in the OAI, but may appear in one of the RT images acquired within the eye. In some embodiments, the processor is configured to display the position of the surgical tool unobstructed, by simultaneously displaying, on the AR display, the OAI out of the ROI and the respective RT image on the ROI. In such embodiments, the processor is configured to visualize the estimated position of the surgical tool in the ROI.

The disclosed techniques improve the quality of a medical procedure carried out in an organ, by visualizing a hidden section of a medical instrument operated within a ROI of the organ.

System Description

Figure 1:
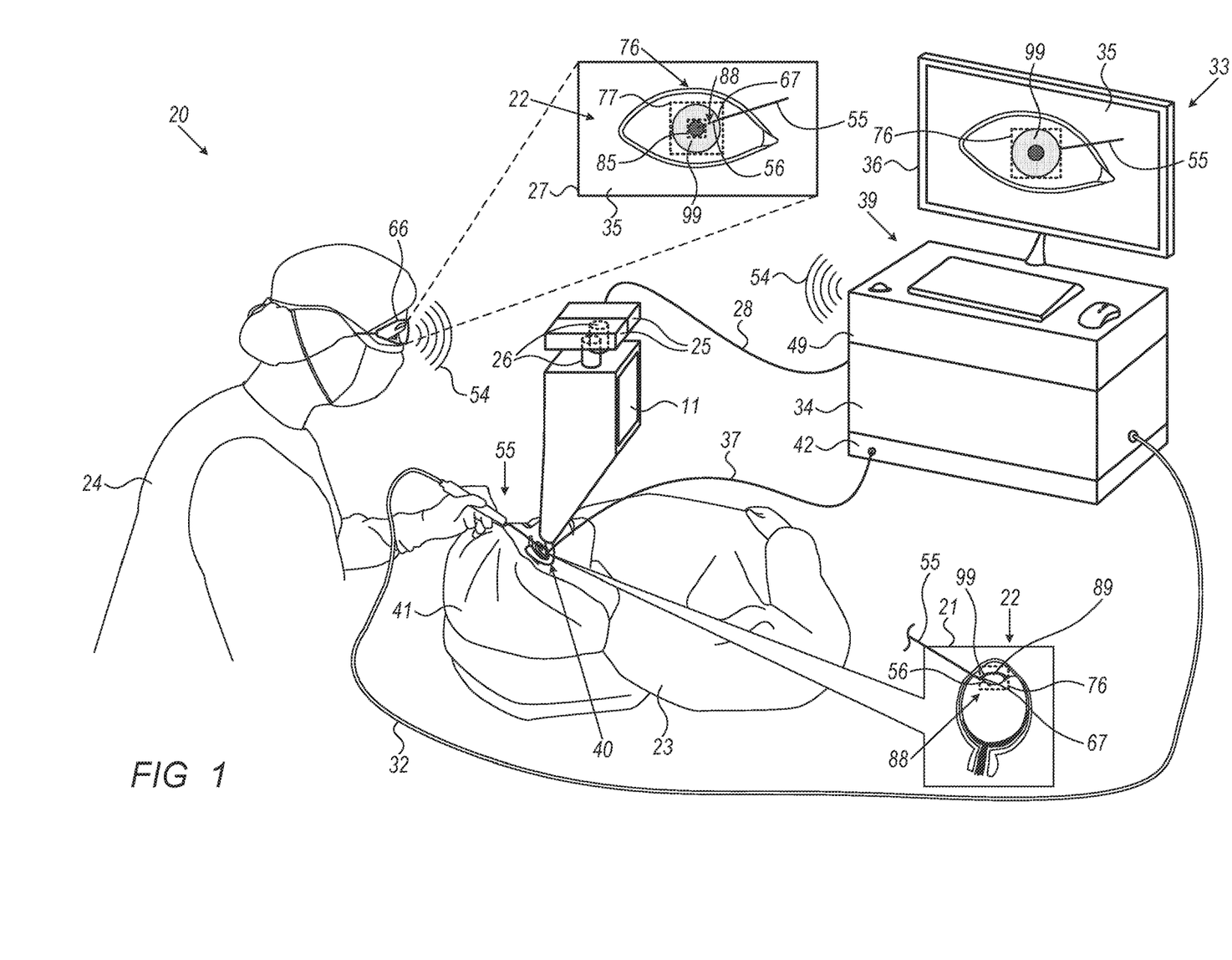
FIG. 1 is a schematic pictorial illustration of an ophthalmic surgical system, in accordance with an embodiment of the present invention.

FIG. 1 is a schematic pictorial illustration of an ophthalmic surgical system 20, in accordance with an embodiment of the present invention. System 20 is configured to carry out various types of ophthalmic procedures, such as but not limited to a cataract surgery.

In some embodiments, system 20 comprises a medical instrument, such as but not limited to a phacoemulsification handpiece or any other suitable type of an ophthalmic surgical tool, referred to herein as a tool 55, used by a surgeon 24 to carry out the ophthalmic surgical procedure. Other surgical tools may comprise an irrigation and aspiration (I/A) handpiece, a diathermy handpiece, a vitrectomy handpiece, and similar instruments.

Reference is now made to an inset 21 showing a sectional view of the surgical procedure carried out in an eye 22 of a patient 23. In some embodiments, surgeon 24 applies tool 55 for treating eye 22, in the present example, surgeon 24 inserts a distal end 88 of tool 55 into a region-of-interest (ROI) 76 of eye 22. In the example of inset 21, during a cataract surgical procedure, surgeon 24 inserts tool 55 below iris tissue 99 so as to apply phacoemulsification to the lens 89 of eye 22.

In some embodiments, tool 55 comprises one or more position sensors 56 of a position tracking system (PTS), and a camera 67, both are described in detail below. At least one position sensor 56 may comprise a triple-axis sensor (TAS) made from three coils or a single-axis sensor (SAS) implemented on a printed circuit board (PCB) or using any other suitable technique. Magnetic position sensors are described in further detail, for example in U.S. Pat. Nos. 6,498,944 and 6,690,963, and in U.S. patent Publication No. 2018/0228392, whose disclosures are all incorporated herein by reference. The one or more sensor(s) 56 may be located anywhere on tool 55, for example, anywhere on a shaft of the tool or a portion of the tool located near the treatment site. In the present example, position sensor 56 and camera 67 are both coupled with distal end 88 of tool 55.

In some embodiments, camera 67 is configured to acquire real-time (RT) images of distal end 88 and a section of eye 22 in close proximity to distal end 88, for example, at least part of ROI 76. In such embodiments, camera 67 and tool 55 are configured to transfer the acquired images, via a cable 32, in RT to processor 34 and/or to any other processor of system 20 as will be described below.

In the context of the present disclosure and in the claims, the term real-time (RT) refers to any time frame up to ½s of a second for (a) acquiring one or more images, using camera 67 and/or by any other camera inserted into eye 22, and (b) receiving the one or more acquired images by processor 34 or any other processor of system 20. In other embodiments the term real-time may refer to any other suitable range of time depending on the hardware of the related components of system 20. For example, the image acquisition time of cameras 67 and 78, and the computational speed of processor 34, and other electronic devices of system 20.

Reference is now made back to the general view of FIG. 1. In some embodiments, system 20 comprises a location pad 40 having a frame and a plurality of field-generators shown and described in detail in FIG. 3 below. In some embodiments, location pad 40 comprises a flexible substrate, which is configured to be attached to facial tissue (e.g., skin) of patient 23. In the context of the present disclosure, and in the claims, using the term "attached" means that, when head 41 of patient 23 is moved in a given offset, location pad 40 is moved in the same offset. In other words, location pad 40 and head 41 are considered to be a single rigid body In an embodiment, system 20 comprises the aforementioned magnetic position tracking system, which is configured to track the position of one or more position sensors, such as position sensor 56 located on tool 55 that is used for treating eye 22, and/or other position sensors coupled to tools inserted into head 41, eye 22, or into any other organ of patient 23. In an embodiment, the magnetic position tracking system comprises magnetic field-generators (not shown) fixed at respective positions of the aforementioned frame of location pad 40, whose details are shown and described in FIG. 3 below.

In some embodiments, position sensor 56 is configured to generate one or more position signals in response to sensing external magnetic fields generated by the field-generators of location pad 40. In some embodiments, a processor 34 (described in detail below) of system 20 is configured to estimate, based on the position signals, the position of tool 55, e.g. distal end 88, within ROI 76 of eye 22.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Publication Nos. 2002/0065455 A1, 2003/0120150 A1 and 2004/0068178 A1, whose disclosures are all incorporated herein by reference.

In some embodiments, system 20 comprises a console 33, which comprises a memory 49, and a driver circuit 42 configured to drive, via a cable 37, the field-generators with suitable signals so as to generate magnetic fields in a predefined working volume, such as in ROI 76 of eye 22.

In some embodiments, console 33 comprises processor 34, typically a general-purpose computer, with suitable front end and interface circuits for receiving the position signals from position sensor 56 coupled to tool 55. In the present example, processor 34 receives the position signals via cable 32, and may use cable 32 for receiving the aforementioned RT images from camera 67 and for exchanging any suitable signals with other components of tool 55. Other means of transmitting and receiving signals known in the art are also contemplated, e.g. BLUETOOTH or other wireless connection. Console 33 further comprises input devices 39 and a display 36 (which may also be, for example, a keyboard, touch screen graphical user interface, or the like).

In some embodiments, system 20 comprises an ophthalmic surgical microscope 11, such as ZEISS OPMI LUMERA series or ZEISS ARTEVO series supplied by Carl Zeiss Meditec AG (Oberkochen, Germany), or any other suitable type of ophthalmic surgical microscope provided by other suppliers. Ophthalmic surgical microscope 11 is configured to produce stereoscopic optical-based anatomical images and two-dimensional (2D) optical-based anatomical images of eye 22. In some embodiments, system 20 comprises two cameras 25 coupled, respectively, to two eyepieces 26 of ophthalmic surgical microscope 11, and configured to acquire two respective optical-based anatomical images displaying the anatomy of eye 22.

In some embodiments, the coupling between cameras 25 and eyepieces 26 may be carried out using a suitable jig, or any other suitable method and/or apparatus.

In some embodiments, processor 34 is configured to receive the optical-based anatomical images from cameras 25, via a cable 28 (or any other suitable means of transmitting and receiving signals known in the art), and, based on the received images received from cameras 25, to display an optical-based anatomical image, referred to herein as an image 35, on display 36. Note that processor 34 is configured to display in image 35: (i) a stereoscopic image by using two separate optical paths with two objectives and eyepieces 26 to provide slightly different viewing angles to two respective cameras 25, or (ii) a 2D optical-based anatomical image, e.g., by using an optical-based anatomical image received from one selected camera 25 of system 20. Note that in most cases surgeon 24 may prefer using the stereoscopic image in such surgical applications.

As shown in the sectional view of inset 21, surgeon 24 inserts distal end 88 of tool 55 below iris tissue 99. Therefore, iris tissue 99 constitutes a blocking element for imaging distal end 88 in image 35. In other words, by looking at image 35 on display 36, surgeon 24 cannot see the location of distal end 88 due to the blocking element within ROI 76, so as to safely and accurately emulsify the lens of eye 22.

In some embodiments, processor 34 is configured to receive, from an anatomical imaging system, such as but not limited to a computerized tomography (CT) system (not shown), a three-dimensional (3D) CT-based anatomical image acquired prior to the ophthalmic procedure.

In some embodiments, system 20 comprises an optical head mount display (HMD) 66 using augmented reality techniques for visualizing distal end 88 of tool 55 overlaid on at least one anatomical image, as described herein.

Reference is now made to an inset 27 showing a displayed augmented image described herein. In an embodiment, processor 34 is configured to select, from the 3D anatomical image, a 2D slice of the anatomical image comprising CT imaging of ROI 76, referred to herein as a CT image (CTI) 77. Note that processor 34 is configured to display at least two types of anatomical images: (a) image 35, which is an optical-based anatomical image based on images received from ophthalmic surgical microscope 11, and (b) CTI 77, which is a CT-based anatomical based on images received from the CT system. Therefore, in the context of the present disclosure and in the claims, the term "anatomical image" refers to at least one of the optical-based anatomical image and CT-based anatomical image described above.

In some embodiments, processor 34, or any other processor of system 20, is configured to display on HMD 66, RT images 85 acquired by camera 67. Note that RT images 85 may comprise distal end 88 and the surrounding tissues of eye 22.

As described above, distal end 88 of tool 55 may be invisible in image 35, for being obstructed by a blocking element (e.g., iris tissue 99, any other tissue, or a medical apparatus used in the ophthalmic procedure). In some embodiments, based on (a) the position signal received from position sensor 56, (b) one or more RT images 85 received from camera 67, and optionally (c) at least one of the anatomical images (e.g., image 35 and/or CTI 77), processor 34 is configured to display the position of distal end 88 unobstructed. Note that processor 34 may display the position of distal end 88 unobstructed solely based on one or more of the RT images and the position signal received from one or more position sensor(s) 56.

In the example of inset 27, processor 34 is configured to display (a) RT image 85 within ROI 76, (b) CTI 77 in the remaining sections of ROI 76, (c) a visualization of a section of distal end 88 overlaid on CTI 77, and (d) image 35 on all other sections surrounding ROI 76.

In other embodiments, processor 34 or any other processor of system 20, is configured to display on the display of HMD 66 (a) RT image 85 within ROI 76, and (b) image 35 in all sections of eye 22 that are not acquired in RT image 85. Based on the position signal received from position sensor(s) 56, processor 34 or any other processor of system 20, is configured to align between images 35 and 85, such that image 35 is displayed on all sections of eye 22 that are not covered by RT image 85. Note that in these embodiments, processor 34, or any other processor of system 20 (e.g., a processor of HMD 66), is configured to display, in the augmented image, RT images 85 received from camera 67 and image 35, which may be also acquired in real-time, by RT ophthalmic surgical microscope 11, and to align between the RT images based on the position signals received from position sensor(s) 56, as described above.

In some embodiments, HMD 66 and console 33 have wireless devices (not shown) configured to exchange wireless signals 54 for transferring, inter alia, the aforementioned augmented image and/or any suitable combination of image 35, CTI 77, and the position signals of position sensor(s) 56.

In an embodiment, processor 34 is configured to display, on HMD 66, a visualization of distal end 88 overlaid on any of the augmented images described above. In the example of inset 27, processor 34 is configured to replace, in ROI 76, the section of the image 35 image 35 with a corresponding CTI 77 and with RT image 85.

In some embodiments, processor 34 is configured to register at least image 35 image 35 and RT image 85 in a common image, such as a coordinate system of the position tracking system. In other words, processor 34 receives the following inputs: (a) the anatomical image from at least one of ophthalmic surgical microscope 11 and the CT system, (b) RT image 85 from camera 67, and (c) the position signal (generated by position sensor 56) from the position tracking system. Subsequently, processor 34 processes at least some of the received three inputs, for example, by producing image 35 image 35, and/or RT image 85, and registers the coordinate systems of image 35 image 35, RT image 85 and the position signal(s) received from position sensor(s) 56, in a common coordinate system (e.g., the coordinate system of the position tracking system).

In some embodiments, after performing the registration process described above, processor 34 is configured to track the position of distal end 88, based on position signals received from one or more position sensor(s) 56. Moreover, processor 34 is configured to display or visualize the position of distal end 88 overlaid on at least one of the registered RT image 85, optionally CTI 77, and image 35 image 35. In the example of inset 27, processor 34 is configured to produce the aforementioned augmented image comprising: (a) RT image 85 having distal end 88 displayed on at least part of ROI 76, (b) CTI 77, (c) image 35 image 35 displaying tool 55 and eye 22 surrounding the section covered by RT image 85, and (d) a visualization of distal end 88, overlaid on CTI 77 in the sections of ROI 76 not covered by RT image 85. In the context of the present disclosure and in the claims, the terms "produce" and "generate" are used interchangeably, e.g., for signals and images made by one or more position sensors 56, processor 34 and any other component of system 20.

In some embodiments, processor 34 is configured to transmit the augmented image (e.g., the augmented image shown in inset 27, or the augmented image comprising solely RT image 85 and image 35) described above, to HMD 66 so that surgeon 24 can see eye 22 and a visualization of the estimated position of distal end 88 of tool 55.

In some embodiments, the augmented image shown in inset 27, provides surgeon 24 with a complete visualization of tool 55, including distal end 88. In other embodiments, in order to optimize the visualization of distal end 88 during the ophthalmic procedure, processor 34 is configured to dynamically control the size of ROI 76, automatically (e.g., based on the position and/or obstruction of distal end 88) or in response to an instruction received from surgeon 24 using input device 39.

In alternative embodiments, HMD 66 may comprise a processor (not shown), which is configured to carry out at least some of the operations carried out by processor 34 and described above. In such embodiments, at least some of the signals described above (e.g., optical images from ophthalmic surgical microscope 11, CTI 77 from processor 34 or the CTI from the CT system, the position signals from position sensor(s) 56) may be transmitted directly (wirelessly or via cables) to the processor of HMD 66, which may generate and display the augmented image on HMD 66. In yet other embodiments, the operations described above may be divided, using any suitable definition, between processor 34 and the processor of HMD 66, so that the augmented image is displayed on HMD 66 as described in detail above.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of ophthalmic and other minimally invasive and surgical systems.

Figure 2:
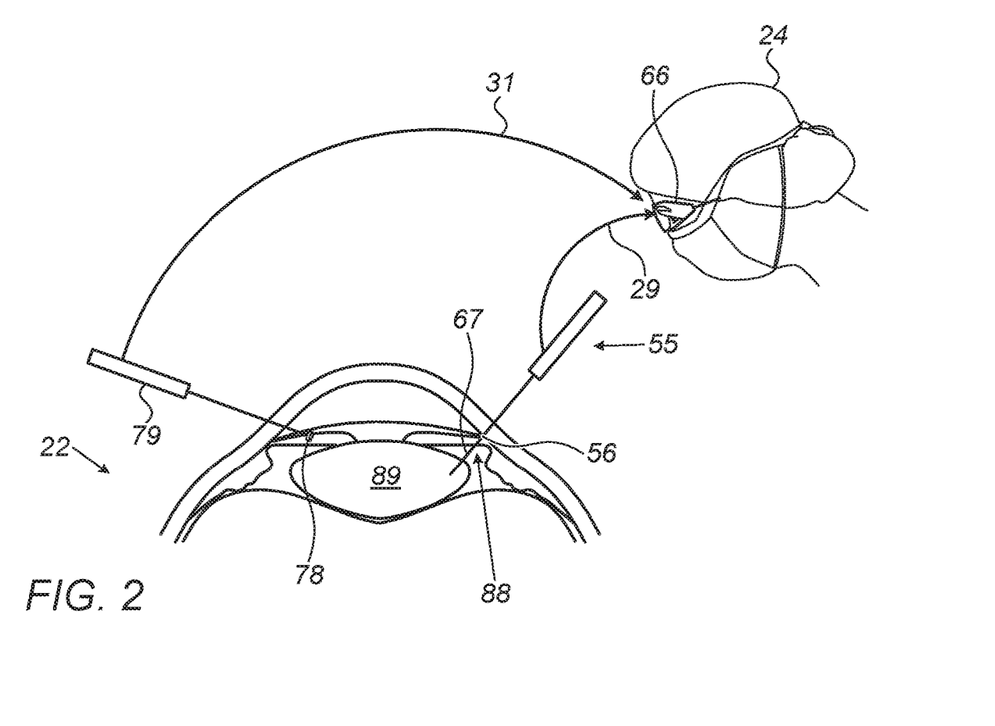
FIG. 2 is a schematic sectional view of an ophthalmic surgical procedure, in accordance with another embodiment of the present invention.

Augmented Reality Imaging Using Real-Time Images Acquired by Camera Inserted into Patient Eye FIG. 2 is a schematic sectional view of an ophthalmic surgical procedure carried out by surgeon 24 using system 20, in accordance with another embodiment of the present invention. In the example of FIG. 2 the ophthalmic surgical procedure comprises a phacoemulsification cataract surgery. In some embodiments, tool 55 comprises an ultrasonic device configured to break up and then remove a cloudy lens 89, referred to as cataract, from eye 22 to improve vision. Subsequently, surgeon 24 inserts an intraocular lens (IOL) (not shown) that replaces lens 89.

During the cataract surgery, surgeon 24, or an assisting operator of system 20, inserts into eye 22, a tool 79 have a camera 78 fitted at the distal end of tool 79. In some embodiments, camera 78 is configured to transmit RT images, of distal end 88 and surrounding eye tissues, to the processor (not shown) of HMD 66, and/or to processor 34. In the example of FIG. 2, the RT images acquired by camera 78 are transmitted directly to HMD 66, via a wired or wireless communication channel, referred to herein as a channel 31.

In case the RT image acquired by camera 78 is not sufficiently clear and/or not capturing a sufficiently large portion of distal end 88, surgeon 24 may adjust the position of camera 78 within eye 22, by moving tool 79.

In some embodiments, tool 55 is configured to transfer the position signal(s) generated by position sensor(s) 56, to the processor of HMD 66, via a wired or wireless communication channel, referred to herein as a channel 29.

In some embodiments, the processor of HMD 66 (and/or processor 34) is configured to register between the RT image acquired by camera 78 and at least the position signal of position sensor(s) 56 in a common coordinate system, e.g., the coordinate system of the PTS.

Figure 3:
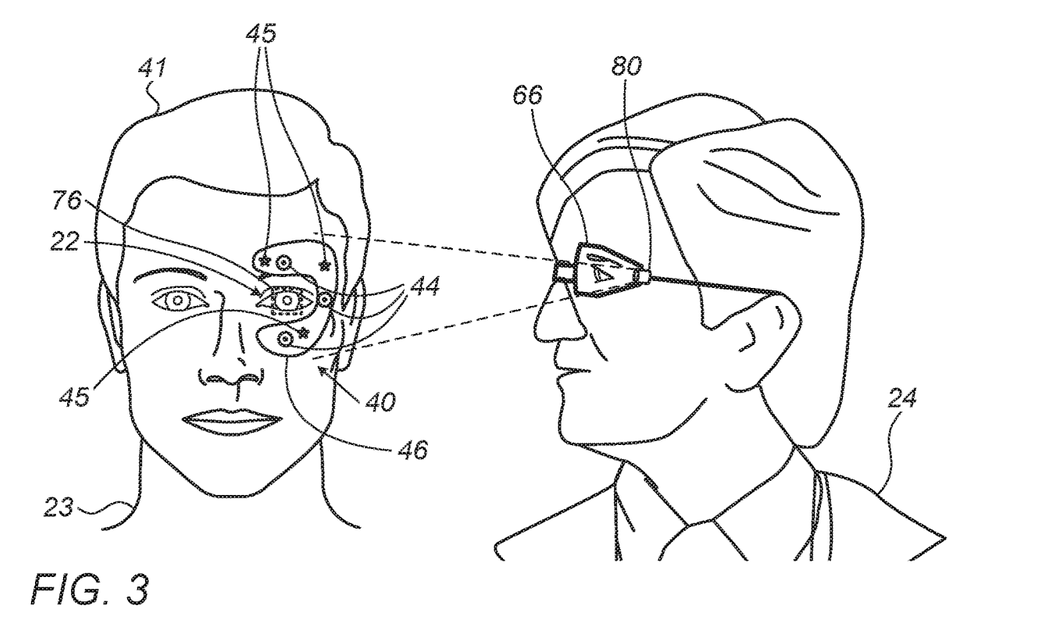
FIG. 3 is a schematic pictorial illustration of a location pad used for tracking a medical instrument treating a patient eye, in accordance with an embodiment of the present invention.
Figure 4:
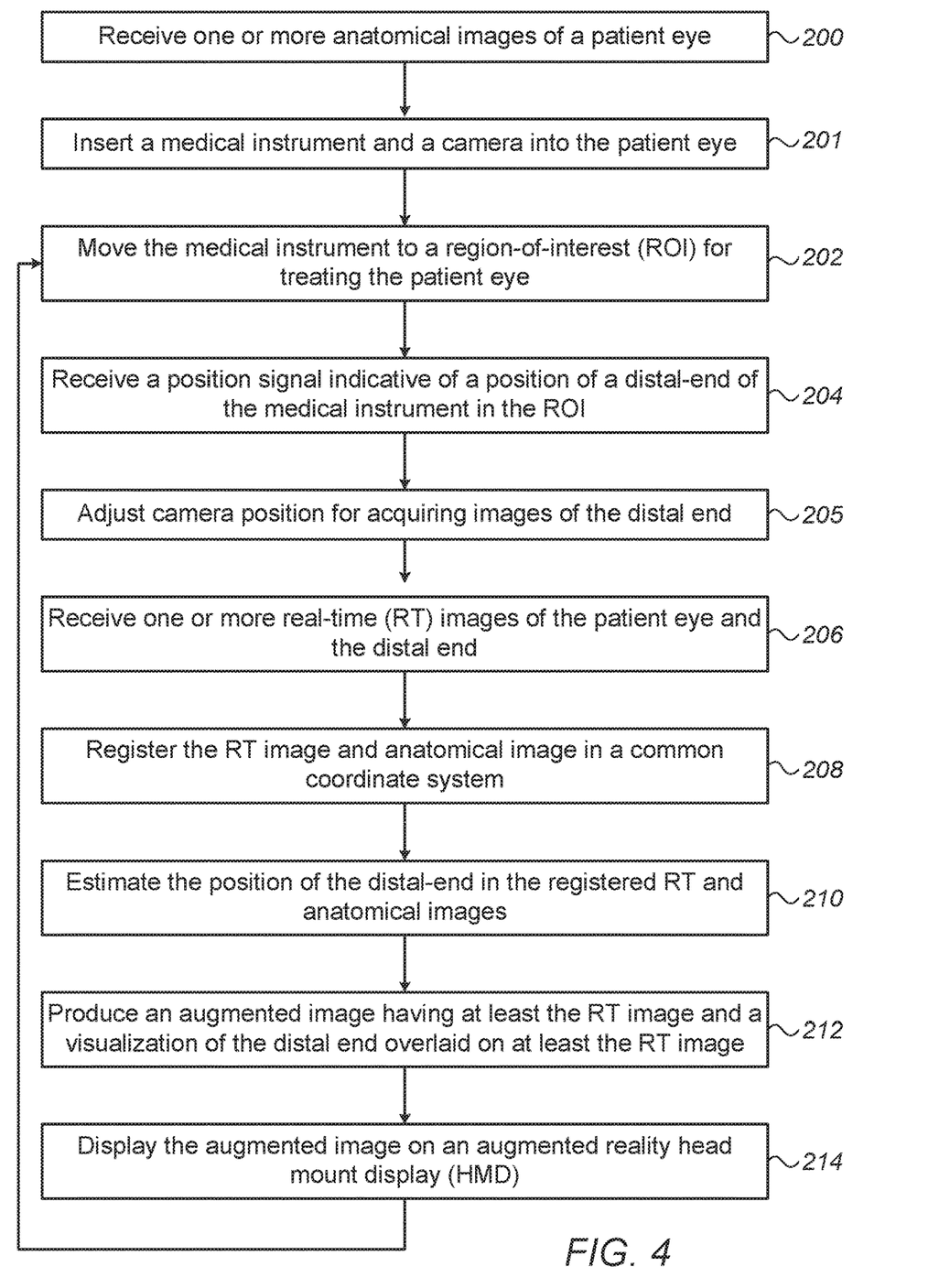
FIG. 4 is a flow chart that schematically illustrates a method for augmented-reality visualization of an ophthalmic surgical tool, in accordance with an embodiment of the present invention.

In the description of FIGS. 2, 3 and 4 below, the term "the processor" refers to herein as the processor of HMD 66 and/or processor 34. In some embodiments, the processor is configured to register the RT image acquired by camera 78 and the position signal(s) of position sensor(s) 56 with one or more of the other images described in FIG. 1 above, such as RT image 85, image 35, and CTI 77.

In some embodiments, using the techniques described in FIG. 1 above, the processor is configured to produce an augmented reality image having (a) at least one of the RT images received from cameras 67 and 78, or any suitable combination thereof, displaying a given section surrounding distal end 88, and (b) image 35 in the sections of eye 22 that are surrounding the given section. In some embodiments, based on the position signal(s) of position sensor(s) 56, the processor is configured to align the aforementioned images comprising the augmented reality image. In such embodiments, the processor is configured to display, on HMD 66, a continuous image comprising at least part of eye 22, together with tool 55 and distal end 88, in the augmented reality image. In the context of the present disclosure and in the claims, the term "continuous" refers to a seamless image produced from two or more different images and covers all sections of interest of eye 22.

In other embodiments, using the augmented reality techniques described above, the processor is configured to display a section of the augmented image (e.g., a section comprising iris tissue 99 or any other blocking element) transparent. Subsequently, the processor is configured to overlay and register at least a clip of one or more of the RT images (received from cameras 67 and/or 78) on the transparent section in the augmented image. Note that the clip or image size is typically identical to the size of the transparent section, so as to display the continuous image as described above.

In some embodiments, based on the augmented reality image, surgeon 24 may position distal end 88 at an optimal position for performing the phacoemulsification cataract surgery. Moreover, after breaking-up and removing cloudy lens 89, the processor is configured to display on HMD 66 and suitable image for verifying the all parts of cloudy lens 89 were removed and that eye 22 is ready for implanting the IOL replacing lens 89. For example, the processor may display at least one of the RT images received from cameras 67 and/or 78, or a combination thereof in a subsequent augmented reality image. In another example, the processor may add image 35 to the subsequent augmented reality image, so as to provide surgeon 24 with a larger field-of-view of eye 22.

In the embodiments described in FIG. 2, before breaking-up and removing lens 89, the processor is configured to display the augmented reality image having at least distal end 88 and lens 89, based on two or more RT images selected, for example, from the aforementioned RT images received from cameras 67 and 78, and image 35. In such embodiments, the processor may not have to overlay a marker, indicative of the position of distal end 88, on one or more of the registered images, because the augmented reality image already comprises one or more RT images of distal end 88 and tool 55.

Additionally or alternatively, the processor is configured to visualize the position of distal end 88 on CTI 77, as described in FIG. 1 above, so as to provide surgeon 24 with an indication of the actual position of distal end 88, e.g., before starting to break-up lens 89.

This particular configuration of system 20 is shown in FIG. 2 by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of surgical systems.

In other embodiments, a combination of image 35, the RT image produced by camera 78 and the position signal from position sensor 56, may be sufficient for producing the augmented reality image providing surgeon 24 with sufficient information to carry out the phacoemulsification cataract surgery. In such embodiments, camera 67 may be omitted from the configuration of system 20, and CT imaging may not be needed, thus avoiding redundant X-ray radiation applied to head 41 of patient 23.

Improving Position Tracking Accuracy Using a Location Pad Surrounding Treated Eye FIG. 3 is a schematic pictorial illustration of location pad 40 used for tracking tool 55 when treating eye 22, in accordance with an embodiment of the present invention. In some embodiments, location pad 40 comprises a frame 46 made from a flexible substrate, such as a flexible printed circuit board (PCB), and a plurality of field-generators 44 coupled with frame 46.

In some embodiments, frame 46 is attached to tissue (e.g., cheek and forehead) that is at least partially surrounding eye 22 and is configured to place a plurality of field-generators 44 at respective positions surrounding ROI 76. In some embodiments, each field-generator 44 comprises one or more coils arranged in any suitable configuration, e.g., concentric or non-concentric arrangement. Several configurations of field-generators are implemented in various types of location pads, and are described in detail, for example, in U.S. Patent Publication Nos. 2007/0265526, US2017/0007156, and in U.S. Pat. No. 8,180,430, whose disclosures are all incorporated herein by reference.

In the exemplary configuration shown in FIG. 1, pad comprises three field-generators 44, but may alternatively comprise any other suitable number of field-generators 44.

As described in FIG. 1 above, the magnetic position tracking system comprises magnetic field-generators 44 fixed at respective positions of frame 46 of location pad 40. Position sensor 56 is configured to generate one or more position signals in response to sensing external magnetic fields generated by the field-generators 44 of location pad 40, and processor 34 (and/or the processor of HMD 66) is configured to estimate, based on the one or more position signals, the position of distal end 88 within ROI 76 of eye 22.

In principle, it is possible to use any suitable type of location pad having field-generators generating respective magnetic fields at least in ROI 76. For example, U.S. Patent Publication No. 2018/0098816, whose disclosure is incorporated herein by reference, describes a location pad surrounding head 41 used for ear-nose-throat (ENT) applications. Such location pads, however, do not enable positioning accuracy sufficient for performing a cataract surgical procedure, mainly because of insufficient proximity between the field-generators and the ROI in which the surgeon performs the procedure. For example, a cataract surgery procedure requires a sub-millimeter positioning accuracy, which can be obtained when field-generators 44 are positioned in close proximity to ROI 76. Moreover, any movement of head 41 may spoil the registration between image 35, the RT images of cameras 67 and 78, CTI 77 and position signals produced by position sensor 56, and therefore may degrade the quality of the cataract surgical procedure.

In some embodiments shown in FIG. 3, location pad 40 is attached to and conforms to the skin surrounding at least part of eye 22. Therefore, location pad 40 moves together with head 41, so that any movement of head 41 may not spoil the registration described in FIG. 1 above.

In some embodiments, the close proximity between ROI 76 and the surrounding field-generators 44 improves the positioning accuracy of the position sensor(s) 56 in the coordinate system of the position tracking system. The improved positioning accuracy results in improved overlay accuracy of distal end 88 visualized on the augmented image described in FIG. 1 above, and/or the overlay accuracy in at least one of image 35 and one or more of the RT images of cameras 67 and 78.

In some embodiments, location pad 40 comprises one or more tracking elements 45 for registering location pad 40 with eye 22. In the example of FIG. 3, tracking elements 45 comprise optical tracking elements, such as infrared light emitting diodes (LEDs), each of which having a different flashing rate.

In some embodiments, HMD 66 comprises an image sensor 80, which is configured, to acquire images of the LEDs of tracking elements 45, and to send the images to a respective processor. In the example of FIG. 1 above, the images acquired by image sensor 80 may be conveyed by wireless signals 54 to processor 34. In the example of FIG. 2 above, the images acquired by image sensor 80 may be conveyed by channel 29 to the processor of HMD 66. In an embodiments, the images acquired by image sensor 80 may be conveyed to both processors.

In some embodiments, based on the received images of the tracking elements 45, the processor is configured to dynamically update (e.g., in real-time) the registration between ROI 76 and the coordinate system of the PTS (or any other common coordinate system). The real-time registration may improve the quality of the cataract surgical procedure, by improving the accuracy and visualization of the estimated position of distal end 88 in ROI 76.

In other embodiments, location pad 40 may comprise any other suitable type of LEDs or other sorts of tracking elements. Moreover, in the example of FIG. 3, location pad comprises three tracking elements 45, but in other embodiments, location pad 40 may have any other suitable number tracking elements 45, typically but not necessarily, arranged around eye 22.

This particular configuration of location pad 40 is shown by way of example, in order to illustrate certain alignment and/or registration problems that are addressed by embodiments of the present invention and to demonstrate the application of these embodiments in enhancing the performance of system 20. Embodiments of the present invention, however, are by no means limited to this specific sort of example location pad and/or system, and the principles described herein may similarly be applied to other sorts of location pads and/or medical systems. For example, in FIG. 3 frame 46 has a horseshoe shape partially surrounding eye 22 and open at the side of the patient nose, in other embodiments, frame 46 may have any other suitable shape, e.g., a bagel-shape fully surrounding eye 22, or a goggles-shape or eye-mask shape comprising two bagel-shaped frames fully surrounding both eyes of patient 23.

Moreover, in some embodiments, a substantially identical location pad 40 may be flipped 180° for being used on the second eye of patient 23. In other embodiments, a location pad for the second eye may have a horseshoe shape open at the side of the patient nose, e.g., having a symmetric configuration to that of location pad 40.

In other embodiments, the location pad frame may have any other suitable shape and may have any suitable number of at least field-generators 44 at suitable respective positions. In such embodiments, the location pad may have only field-generators 44 fixed on the frame. In alternative embodiments, the location pad may have both field-generators 44 and tracking elements fixed on the frame having any suitable shape.

Augmented Reality Visualization of an Ophthalmic Surgical

Tool FIG. 4 is a flow chart that schematically illustrates a method for augmented-reality visualization of tool 55, in accordance with an embodiment of the present invention. In the description below, the method is implemented on processor 34, but in other embodiments, the method may be implemented, mutatis mutandis, on any other suitable type of computing device or system, such as the processor of HMD 66.

The method begins at an anatomical image receiving step 200, with processor 34 receiving one or more, optical-based, and CT-based anatomical images of patient eye 22. As described in FIG. 1 above, processor 34 produces (a) image 35 based on optical images received from ophthalmic surgical microscope 11, and (b) CTI 77 based on CT images received from the CT system.

At a medical instrument insertion step 201, surgeon and optionally an assisting operator of system 20, insert (a) tool 55, having surgical capabilities and camera 67, and (b) tool 79 having camera 78, as described in FIGS. 1 and 2 above.

At a medical instrument movement step 202, surgeon 24 moves tool 55 to ROI 76 for treating patient eye 22, e.g., for removing the cataract using phacoemulsification described in FIG. 1 above.

At a position signal receiving step 204, processor 34 receives, e.g., from position sensor 56, a position signal indicative of the position of distal end 88 of tool 55 within ROI 76, as described in FIG. 1 above. At a camera positioning step 205, surgeon 24, or the assisting operator of system 20, checks whether distal end 88 appears in the frame of camera 78 sufficiently well for performing the surgical procedure, and if needed, surgeon 24, or the assisting operator adjusts the position of camera 78 using tool 79.

At a RT images receiving step 206, processor 34 receives from at least one of cameras 67 and 78, one or more respective RT images of distal end 88 and surrounding eye tissues of ROI 76, as described in FIGS. 1 and 2 above.

At a registration step 208, processor 34 registers at least one of the RT images received from cameras 67 and 78, with at least one of the anatomical images (e.g., image 35 and/or CTI 77), in a common coordinate system. For example, in the coordinate system of the position tracking system.

At a position estimation step 210, processor 34 estimates, based on the one or more position signals received from position sensor(s) 55, the position of distal end 88 in the registered RT and anatomical images, as described in FIGS. 1 and 2 above.

At an augmented image producing step 212, processor 34 produces the augmented image comprising one or more of the RT images and one or more of the anatomical images, as described in FIGS. 1 and 2 above. As shown in inset 27 of FIG. 1 above, processor 34 is configured to position at least a clip of RT image 85 displaying distal end 88, and anatomical images, such as image 35 and CTI 77, surrounding RT image 85. In some embodiments, based on the position signal(s) received from position sensor(s) 56 and the registration carried out in step 208, the processor is configured to set the size of each image, and to align the images relative to one another so as to produce the augmented image shown in inset 27. Similarly, the processor may produce the augmented image based on (a) the RT image received from camera 78, (b) image 35, and (c) the position signal received from position sensor 56, as described in detail in FIG. 2 above.

In some embodiments, processor 34 is configured to check whether distal end 88 appears (a) in one or more of the RT images received from cameras 67 and 78, and (b) in image 35. In case distal end 88 appears in at least a given image from among the RT images and image 35, processor 34 is configured to select the given image for ROI 76 of the augmented reality image. In case distal end 88 does not appear in any of the RT images and image 35, processor 34 is configured, based on the position signal(s) received from position sensor(s) 56, to visualize the distal end 88 overlay on one or more selected images from among the RT images, image 35 and CTI 77, and to display at least a clip of the selected image and visualized distal end 88, at the position of ROI 76 in the augmented reality image.

At a displaying step 214, processor 34 displays the augmented image (e.g., the image shown in inset 27) on HMD 66 or on any other suitable type of augmented reality display. Note that image 35 also displays tool 55 shown out of ROI 76, therefore, surgeon 24 can see both tool 55 and distal end 88 in the augmented image shown, for example, in inset 27 of FIG. 1 above.

In alternative embodiments of steps 212 and 214, the processor of HMD 66 may produce the augmented image based on (a) the RT image received from camera 78, (b) image 35 received from processor 34 or directly based on one or more images received from ophthalmic surgical microscope 11, and (c) the position signal(s) received from position sensor(s) 56. All signals may be conveyed wirelessly or via a cable. Subsequently, the processor displays the augmented image on the display of HMD 66.

In some embodiments, surgeon 24 may decide to carry out the procedure by placing distal end 88 at more than one location within eye 22. In such embodiments, after displaying step 214, the method may loop back to moving step 202, in which surgeon 24 moves distal end 88 to a different location within eye 22. In these embodiments, the position of the ROI within eye 22, could be updated relative to the original position of ROI 76, in response to the updated position, surgeon 24 moves tool 55 as described in step 202 above, and the method is carried out using, mutatis mutandis, the steps described above.

In some embodiments, after breaking up and evacuating lens 89 from eye 22, surgeon 24 may use at least one of cameras 67 and 78 for inspecting eye 22 and verifying that eye 22 does not have residues of lens 89. After the verification, surgeon 24 may extract tools 55 and 79 out of patient eye 22 and start implanting the IOL in place of the aspirated lens 89.

Note that in some cases, one or more steps of the method described above may be redundant. For example, the cataract surgical procedure may be carried out without receiving anatomical images, simply by receiving the RT images from at least one of cameras 67 and 78. In this example, step 200 is redundant, and one or more of steps 208-214 may be adjusted accordingly. In another example, step 205 may be redundant at least in two cases: (a) when using solely camera 67, which is coupled to tool 55, and therefore, is preset for having distal end 88 within its frame, and (b) when camera 78 already has distal end 88 within its frame.

Although the embodiments described herein mainly address ophthalmic procedures, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a processor, which is configured to:
receive, from a camera inserted into an eye of a patient, at least an optical image of at least a region-of-interest (ROI) of the eye;
receive, from a position tracking system (PTS), a position signal indicative of a position of the medical instrument treating the eye;
register the optical image in a coordinate system of the PTS; and
estimate the position of the medical instrument in the optical image;
dynamically control the size of the ROI automatically, wherein the size of the ROI is based on the estimated position of the medical instrument; and
a display, which is configured to visualize at least the ROI and the medical instrument.

2. The system according to claim 1, wherein the optical image comprises a real-time (RT) image.

3. The system according to claim 1, wherein the camera is coupled with the medical instrument and further comprising a second camera coupled to a tool for inserting the second camera into the eye, and wherein the at least optical image comprises at least one of (a) a first optical image received from the first camera and (b) a second optical image received from the second camera.

4. The system according to claim 1, wherein the processor is configured to receive at least an anatomical image of at least the ROI, and wherein at least part of the medical instrument is obstructed by a blocking element, in at least one of the anatomical image and the optical image, and wherein the processor is configured to display the position of the medical instrument unobstructed.

5. The system according to claim 4, wherein, when at least part of the medical instrument is obstructed, the processor is configured to visualize the medical instrument overlaid on at least one of the anatomical image and the optical image.

6. The system according to claim 4, wherein the anatomical image comprises at least one of: (i) an optical-based anatomical image, and (ii) a computerized tomography-based anatomical image.

7. The system according to claim 4, wherein the display comprises an augmented reality display configured to display an augmented reality image, and wherein the processor is configured to simultaneously display, on the augmented reality display, the optical image on a first section of the augmented reality image, and the anatomical image on a second section of the augmented reality image.

8. The system according to claim 4, wherein, (i) when at least part of the medical instrument is obstructed in the anatomical image, the processor is configured to display the ROI and the medical instrument of the optical image, and (ii) when at least part of the medical instrument is obstructed in the optical image, the processor is configured to display the ROI and the medical instrument of the anatomical image.

9. The system according to claim 4, wherein when at least part of the medical instrument is obstructed in the anatomical image and in the optical image, the processor is configured, based on the position signal, to visualize the estimated position of the obstructed part of the anatomical image, in at least one of the anatomical image and the optical image.

10. A method, comprising:
receiving, from a camera inserted into an eye of a patient, at least an optical image of at least a region-of-interest (ROI) of the eye;
receiving, from a position tracking system (PTS), a position signal indicative of a position of a medical instrument treating the eye;
registering the optical image in the coordinate system of the PTS;
estimating the position of the medical instrument in the optical image;
dynamically control the size of the ROI automatically, wherein the size of the ROI is based on the estimated position of the medical instrument; and
visualizing at least the ROI and the medical instrument.

11. The method according to claim 10, wherein the optical image comprises a real-time (RT) image.

12. The method according to claim 10, wherein receiving at least the optical image comprises receiving at least: (a) a first optical image from a first camera coupled with the medical instrument, and (b) a second optical image from a second camera coupled with a tool for inserting the second camera into the eye.

13. The method according to claim 10, further comprising receiving at least an anatomical image of at least the ROI, and wherein at least part of the medical instrument is obstructed by a blocking element, in at least one of the anatomical image and the optical image, and wherein visualizing at least the ROI and the medical instrument comprises displaying the position of the medical instrument unobstructed.

14. The method according to claim 13, wherein, when at least part of the medical instrument is obstructed, and wherein visualizing at least the ROI and the medical instrument comprises visualizing the medical instrument overlaid on at least one of the anatomical image and the optical image.

15. The method according to claim 13, wherein receiving at least the anatomical image comprises receiving at least one of: (i) an optical-based anatomical image, and (ii) a computerized tomography-based anatomical image.

16. The method according to claim 13, wherein visualizing at least the ROI and the medical instrument comprises simultaneously displaying, on an augmented reality display, the optical image on a first section of an augmented reality image, and the anatomical image on a second section of the augmented reality image.

17. The method according to claim 13, wherein, (i) when at least part of the medical instrument is obstructed in the anatomical image, visualizing at least the ROI and the medical instrument comprises displaying the ROI and the medical instrument of the optical image, and (ii) when at least part of the medical instrument is obstructed in the optical image, visualizing at least the ROI and the medical instrument comprises displaying the ROI and the medical instrument of the anatomical image.

18. The method according to claim 13, wherein when at least part of the medical instrument is obstructed in the anatomical image and in the optical image, visualizing at least the ROI and the medical instrument comprises, based on the position signal, visualizing the estimated position of the obstructed part of the anatomical image, in at least one of the anatomical image and the optical image.

* * * * *